US008876766B2

(12) United States Patent
Holmqvist et al.

(10) Patent No.: US 8,876,766 B2
(45) Date of Patent: Nov. 4, 2014

(54) MEDICAMENT DELIVERY DEVICE

(75) Inventors: Anders Holmqvist, Värmdö (SE);
Magnus Gustafsson, Tullinge (SE);
Stephan Lööf, Sköndal (SE); Jochen Ratjen, Nacka (SE)

(73) Assignee: SHL Group AB, Nacka Strand (SE)

( * ) Notice: Subject to any disclaimer, the term of this patent is extended or adjusted under 35 U.S.C. 154(b) by 408 days.

(21) Appl. No.: 13/515,903

(22) PCT Filed: Nov. 30, 2010

(86) PCT No.: PCT/SE2010/051319
§ 371 (c)(1),
(2), (4) Date: Aug. 6, 2012

(87) PCT Pub. No.: WO2011/075042
PCT Pub. Date: Jun. 23, 2011

(65) Prior Publication Data
US 2013/0096495 A1    Apr. 18, 2013

Related U.S. Application Data

(60) Provisional application No. 61/286,114, filed on Dec. 14, 2009.

(30) Foreign Application Priority Data

Jan. 20, 2010 (SE) ...................... 1050063

(51) Int. Cl.
*A61M 5/00* (2006.01)
*A61M 5/20* (2006.01)
*A61M 5/315* (2006.01)
*A61M 5/24* (2006.01)
*A61M 5/31* (2006.01)

(52) U.S. Cl.
CPC ......... *A61M 5/31566* (2013.01); *A61M 5/2033* (2013.01); *A61M 5/2066* (2013.01); *A61M 5/2448* (2013.01); *A61M 5/31511* (2013.01); *A61M 5/31593* (2013.01); *A61M 5/31596* (2013.01); *A61M 5/3129* (2013.01); *A61M 2005/2073* (2013.01); *A61M 2005/31518* (2013.01)
USPC .......................................... 604/135; 604/207

(58) Field of Classification Search
CPC .............. A61M 5/315; A61M 5/3135; A61M 5/31525; A61M 5/31526; A61M 2005/2073; A61M 2005/31518
USPC ......... 604/131, 134, 135, 187, 207–211, 218, 604/224, 228
See application file for complete search history.

(56) References Cited

U.S. PATENT DOCUMENTS 3,384,080 A * 5/1968 Muller ........................ 604/153
4,313,439 A * 2/1982 Babb et al. .................... 604/28

(Continued)

OTHER PUBLICATIONS

Swedish Patent Office, Int'l Search Report in PCT/SE2010/051319, Mar. 25, 2011.

(Continued)

*Primary Examiner* — Matthew F Desanto
(74) *Attorney, Agent, or Firm* — Piedmont Intellectual Property

(57) ABSTRACT

A medicament delivery device includes a housing with a circle-segment-shaped compartment for a drive unit that moves at least one stopper in a medicament container and that includes a support wheel and central hub on which first and second parallel disks are fixedly attached and interconnected by an abutment cross-wall; spherical members between the abutment wall and adjacent the stopper; a clock spring within the hub with an outer end connected to the hub and an inner end connected to a one-direction-rotatable tubular hub coaxially arranged around a shaft fixedly attached to a housing part; and an activation member connected to the first disk by a hold-and-release mechanism. When the activation member is not depressed, the wheel and spring are held in a tensioned static state, and when the activation member is depressed, the spring and wheel are released and the spherical members are forced against the stopper.

18 Claims, 14 Drawing Sheets

(56) References Cited

U.S. PATENT DOCUMENTS

| | | | |
|---|---|---|---|
| 4,846,797 A | | 7/1989 | Howson et al. |
| 5,261,882 A | * | 11/1993 | Sealfon .......................... 604/135 |
| RE35,249 E | * | 5/1996 | Sealfon .......................... 604/135 |
| 6,482,186 B1 | | 11/2002 | Douglas et al. |
| 7,125,395 B2 | * | 10/2006 | Hommann et al. ........... 604/135 |
| 8,647,303 B2 | * | 2/2014 | Cowe ............................ 604/134 |
| 2004/0054326 A1 | | 3/2004 | Hommann et al. |
| 2013/0296778 A1 | * | 11/2013 | Damgaard-Soerensen et al. ............................... 604/82 |

OTHER PUBLICATIONS

Swedish Patent Office, Written Opinion in PCT/SE2010/051319, Mar. 25, 2011.

* cited by examiner

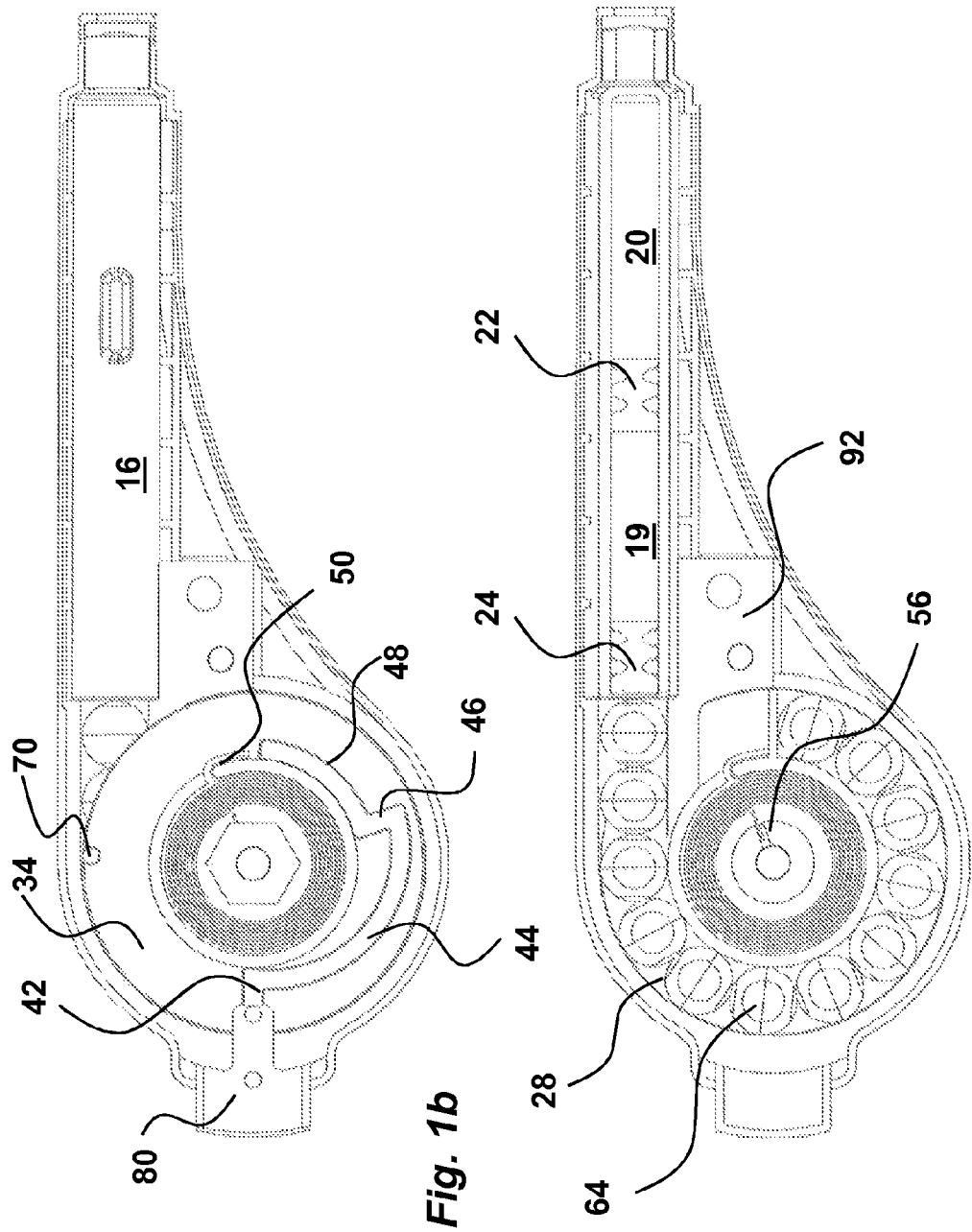

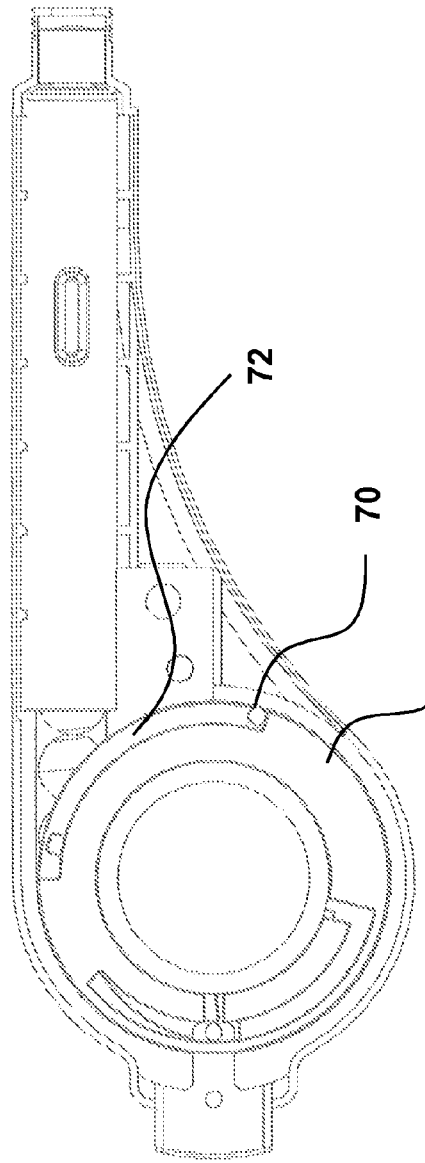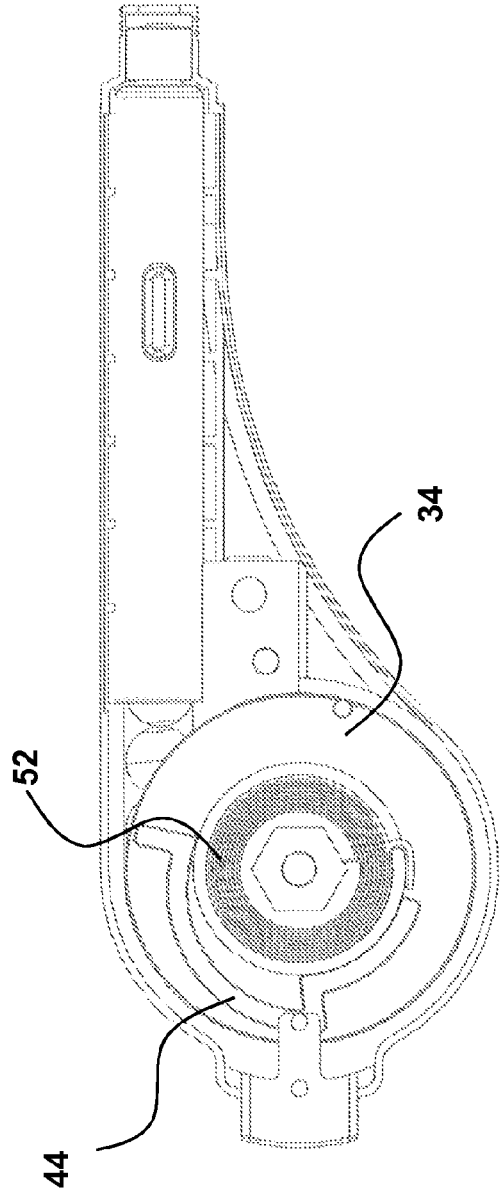
Fig. 7a
Fig. 7b

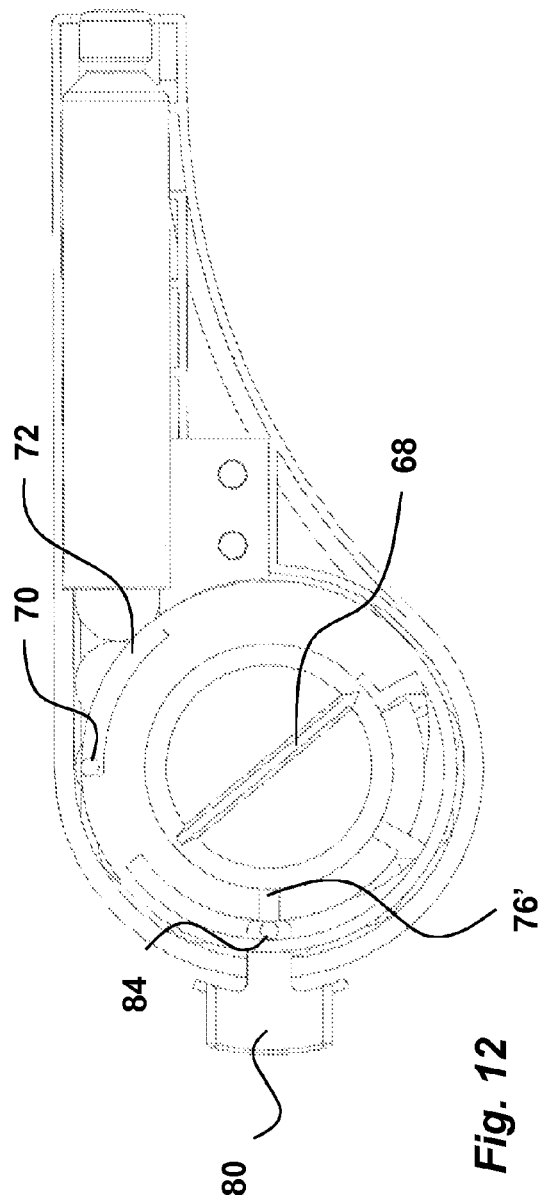
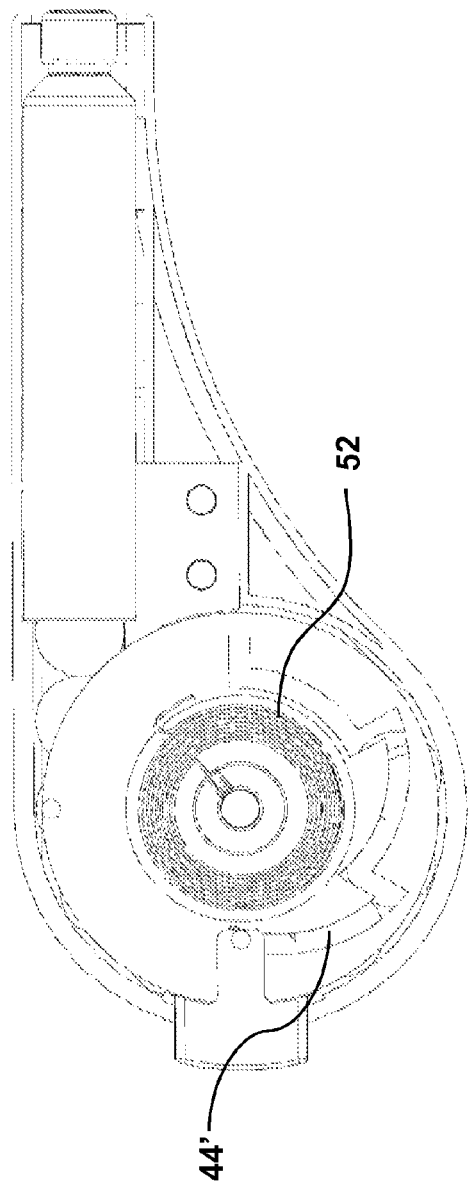
Fig. 12
Fig. 13

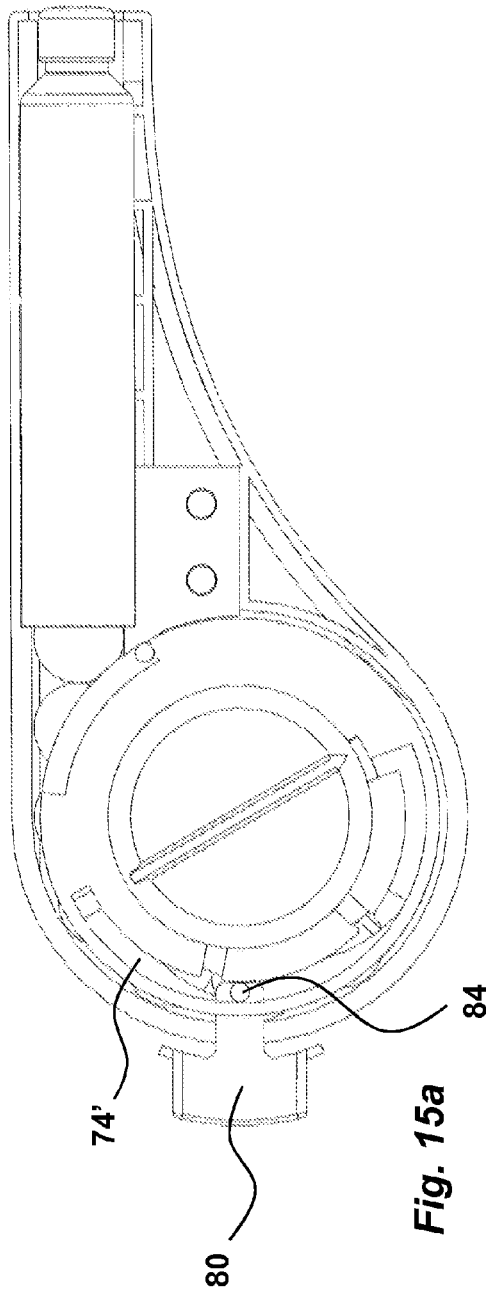
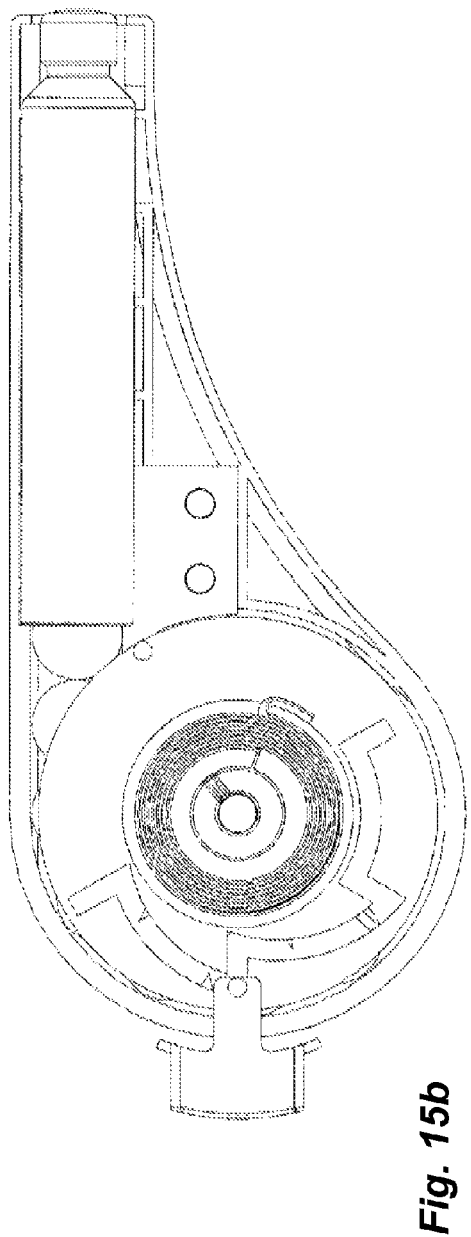
Fig. 15a
Fig. 15b

MEDICAMENT DELIVERY DEVICE

TECHNICAL AREA

The present invention relates to a medicament delivery device and in particular a medicament delivery device that is compact and simple to handle.

TECHNICAL BACKGROUND

There are numerous medicament delivery devices that have been invented and developed during the years. These devices have been provided with different degrees of functionality and automatic features, such as mixing of medicament components, priming, dose delivery, penetration, just to mention a few.

Many devices are arranged with an elongated plunger rod that acts on stoppers inside a medicament container. The plunger rod is pushed in the distal direction by drive force members that often are spiral compression springs. This configuration means that the device becomes quite long since the spring acts on a distal end of the plunger rod, a so called pen injector.

In many instances the users do not want these elongated pen-type injectors due to their form, and a few attempts have been made to shorten the length of the injector. In the design disclosed in U.S. Pat. No. 4,313,439 the size of the device is the linear dimension of the barrel, the piston rod and the linear dimension of the curved path of the spring-powered spheres, thus resulting in no reduction of the overall size. One alternative design is disclosed in U.S. Pat. No. 5,261,882 disclosing a negator spring powered I.V. pump of compact size resulting from imparting a non-circular, rather than a linear configuration to the negator spring; wherein the non-circular configuration takes up less size or linear dimension. However, the non-linear compartment for said negator spring comprises a first axle member establishing a rotating axis for a centrally disposed circular-shaped spindle having a peripheral surface for supporting movement therealong of plural interconnected spheres serving as a piston rod, and a second axle member establishing a rotating axis for a centrally disposed spool which supports the helical coils of the negator spring; thus also resulting in no optimal reduction of the overall size.

BRIEF DESCRIPTION OF THE INVENTION

The aim of the present invention is to obtain a medicament delivery device which is compact and which contains a number of user-friendly features with a reduced number of components at a reduced cost.

This aim is solved according to the present invention with the features of the independent patent claim. Preferable embodiments of the invention form the subject of the dependent patent claims.

According to a main aspect of the invention it is characterised by a medicament delivery device comprising a housing having a proximal and a distal section formed by a first housing part and a second housing part; a first compartment formed inside said proximal housing section for accommodating a medicament container, which medicament container comprises at least one stopper; a circle-segment-formed second compartment formed inside said distal housing section for accommodating a drive unit capable of moving said at least one stopper in the proximal direction within said medicament container; wherein the drive unit comprises a support wheel rotatably arranged inside said second compartment, said support wheel comprises a central tubular hub on which a first and a second washer-formed disks are fixedly attached, parallel to each other and interconnected by an abutment cross-wall; a plurality of spherical members arranged in a row between the abutment wall and adjacent said stopper, said plurality of spherical members being guided in a channel formed by the inner periphery of the circle-segment-formed second compartment, by the outer periphery of said central tubular hub, by the inner side surfaces of the washer-formed disks and by a guide member; a pre-tensioned clock spring coaxially arranged within said central tubular hub having an outer end connected to said central tubular hub and an inner end connected to a one-direction-rotatable tubular hub coaxially arranged around a shaft fixedly attached to the first housing part; and an activation member interactively connected to said first washer-formed disk by co-acting hold-and-release means such that when said activation member is in a non-depressed position said support wheel and said clock spring are held in at least one tensioned and static state and when said activation member is moved from the non-depressed position to a depressed position, said clock spring and thereby said support wheel are released from their at least one tensioned and static state such that said plurality of spherical members are forced against said at least one stopper.

According to a further aspect of the invention, said hold-and-release means are a first transversal protrusion arranged on a proximally directed tongue of the activation member and a first groove on the side surface of the first washer-formed disk, said first groove comprising at least one first radially directed groove section and at least one first generally circumferentially directed groove section wherein each first radially directed groove section is followed by a first generally circumferentially directed groove section, such that when said first transversal protrusion is positioned in at least one first radially directed groove section, said support wheel and said clock spring are held in at least one tensioned and static state and when said activation member is proximally moved from the non-depressed position to the depressed position, the first transversal protrusion is moved from the at least one first radially directed groove section into the first generally circumferentially directed groove section, whereby the clock spring and thereby the support wheel are released from the at least one tensioned and static state.

According to yet a further aspect of the invention, each first generally circumferentially directed groove section has a certain preset length corresponding to a preset dose quantity.

According to another aspect of the invention, said first groove is arranged with at least two first radially and at least two first generally circumferentially directed groove sections respectively, in succession, wherein the first of said first generally circumferentially directed groove sections is arranged with an increasing radius for forcing said activation member towards the distal direction from its depressed position to its non-depressed position, and wherein the last of said first generally circumferentially directed groove sections is arranged with a constant radius, whereby said activation member is held in the depressed position, indicating that the device is used.

According to yet another aspect of the invention, said first groove is arranged with a plurality of first radially and first generally circumferentially directed groove sections in succession providing the delivery of a plurality of doses of medicament, wherein the firsts of said first generally circumferentially directed groove sections are arranged with an increasing radius for forcing said activation member towards the distal direction from its depressed position to its non-depressed position, and wherein the last of said first generally circum-ferentially directed groove sections is arranged with a constant radius, whereby said activation member is held in the depressed position, indicating that the device is used.

According to a further aspect of the invention, said medicament container comprises two compartments, each compartment containing a substance and being separated by a movable stopper, as well as by a distal stopper, wherein said first generally circumferentially directed groove section enables the clock spring to force the support wheel and the plurality of spherical members to perform a mixing of substances.

According to yet a further aspect of the invention, the device further comprises an activation wheel interactively connected to said activation member by co-acting lock-and-release means such that when said activation member is in the non-depressed position, said lock-and-release means lock said activation member from moving from its non-depressed position to its depressed position.

According to another aspect of the invention, said activation wheel comprises a disk-shaped member arranged adjacent said support wheel, as well as a grip means for turning said activation wheel.

According to yet another aspect of the invention, said lock-and-release means are a second transversal protrusion arranged on the proximally directed tongue of the activation member and a second groove on the side surface of the disk-shaped member, said second groove comprising a second generally circumferentially directed section and at least one second radially directed groove section such that when said second transversal protrusion is positioned in said second generally circumferentially directed section, said activation member is locked, and when second transversal protrusion is positioned in front of one of said second radially directed groove sections, said activation member may be moved from its non-depressed position to its depressed position.

According to a further aspect of the invention, said first washer-formed disk is provided with a third transversal protrusion arranged to act on a cut-out of said disk-shaped member such that when said support wheel is rotated by said clock spring, said third transversal protrusion moves said activation wheel from a position allowing movement of said activation member from its non-depressed position to its depressed position to a position where said activation member is locked.

There are a number of advantages with the present invention. Due to the use of only one axle member establishing a rotating axis for a one-direction-rotatable tubular hub to which a pre-tensioned clock spring is coaxially arranged and in its turn to which a circular-shaped support wheel having a peripheral surface for supporting movement therealong of plural interconnected spheres serving as a piston rod, is arranged; a very compact device with a reduced number of components is obtained and in particular the overall size of the device can be greatly reduced in comparison with many conventional medicament delivery devices.

There is also an advantage to utilize grooves on the support wheel cooperating with at least one protrusion of the activation member, whereby a locking of the support wheel is obtained and wherein the length of a portion of the groove corresponds to a certain dose quantity. In this manner it is possible to vary the dose quantity by altering the length of the groove. It is also then possible to provide a number of doses from the same medicament container, i.e. a multi dose device, by adding groove portions around the support wheel.

Also, when a dual chamber medicament container is used, the first of a succession of groove sections is used for a mixing operation. The groove sections could further be arranged such that the activation member is locked in a certain position, indicating that the device is used and should be discarded. It is thus not possible for a user to mix new and used devices.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIG. 1b is a side view of the embodiment of FIG. 1 with an activation wheel removed for clarity, FIG. 1c is a cross-sectional side view of the device of FIG. 1.

DETAILED DESCRIPTION OF THE INVENTION

Figure 1A:
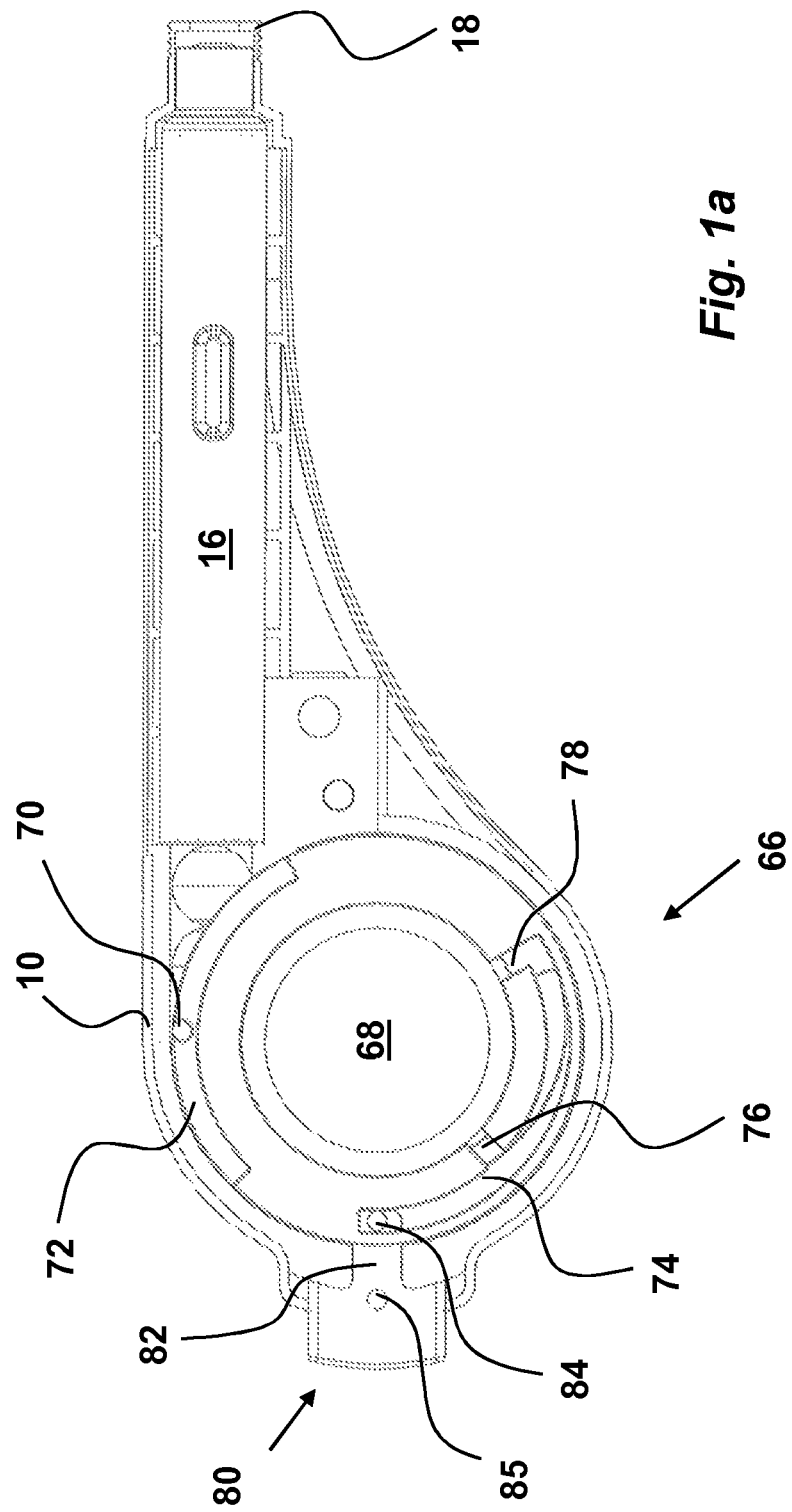
FIG. 1a is a side view of a first embodiment with a housing part of the device removed for clarity.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

FIGS. 1-10 show a first embodiment comprising the present invention and FIGS. 11-14 show a second embodiment where the same components of the first embodiment have the same reference numerals and modified components of the first embodiment have an apostrophe added to the reference numerals.

The present invention relates to a medicament delivery device comprising a housing having a proximal and a distal section formed by a first housing part 10 and a second housing part 12. It is however to be understood that other designs are feasible within the present invention.

The medicament delivery device further comprises: a first compartment 14 formed inside said proximal housing section for accommodating a medicament container 16; 16', wherein a proximal neck portion of the medicament container 16; 16' fits into a threaded neck portion 18 of the proximal end of the housing, and wherein said medicament container comprises at least one stopper 22, 24; 24; and—a circle-segment-formed second compartment formed inside said distal housing section for accommodating a drive unit capable of moving said at least one stopper in the proximal direction within said medicament container 16; 16'. A medicament delivery member (not shown) may be attached to the neck portion 18 of the housing.

The drive unit comprises:—a support wheel 30; 30' rotatably arranged inside said second compartment, said support wheel comprises a central tubular hub 32 on which a first 34; 34' and a second 36 washer-formed disks are fixedly attached, parallel to each other and interconnected by an abutment cross-wall 38;—a plurality of spherical members 64 arranged in a row between the abutment wall 38 and adjacent said stopper 22, 24; 24, said plurality of spherical members 64 being guided in a channel 28 formed by the inner periphery of the circle-segment-formed second compartment, by the outer periphery of said central tubular hub 32, by the inner side surfaces of the washer-formed disks and by a guide member 92;—a pre-tensioned clock spring 52 coaxially arranged within said central tubular hub 32 having an outer end connected to said central tubular hub 32 and an inner end connected to a one-direction-rotatable tubular hub 54 coaxially arranged around a shaft 58 fixedly attached to the first housing part 10; and—an activation member 80 interactively connected to said first washer-formed disk 34 by co-acting hold-and-release means such that when said activation member is in a non-depressed position said support wheel and said clock spring are held in at least one tensioned and static state and when said activation member is moved from the non-depressed position to a depressed position, said clock spring and thereby said support wheel are released from their at least one tensioned and static state such that said plurality of spherical members 64 are forced against said at least one stopper 24.

Figure 2:
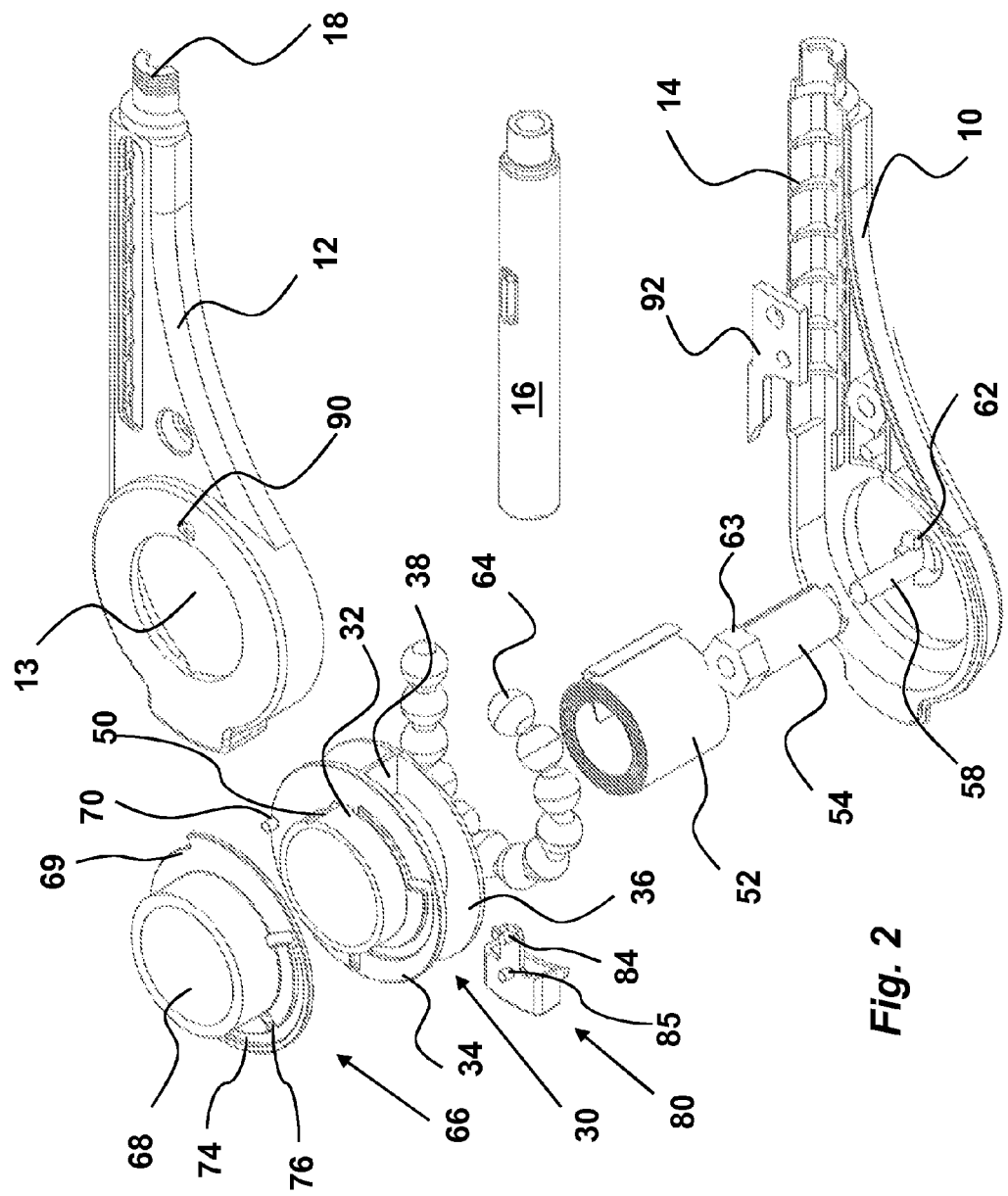
FIG. 2 is an exploded view of the device of FIG. 1.

As seen in FIGS. 1b and 2, the hub 32 is arranged with a slit 50 into which the outer end of the clock spring 52 is fitted and fastened. The inner end of the clock spring 52 is attached to a slit 56 of the one-direction-rotatable tubular hub 54. One end of the one-direction-rotatable tubular hub 54 is provided with sloping wedge-shaped surfaces 60, FIG. 3, which cooperate with corresponding sloping wedge-shaped surfaces 62, FIG. 2, on the inner surface of the distal section of the first housing part 10 surrounding the shaft 58. The function of the wedge-shaped surfaces 60, 62 will be explained below. The other end of the one-direction-rotatable tubular hub 54 is arranged with a head 63.

Figure 3:
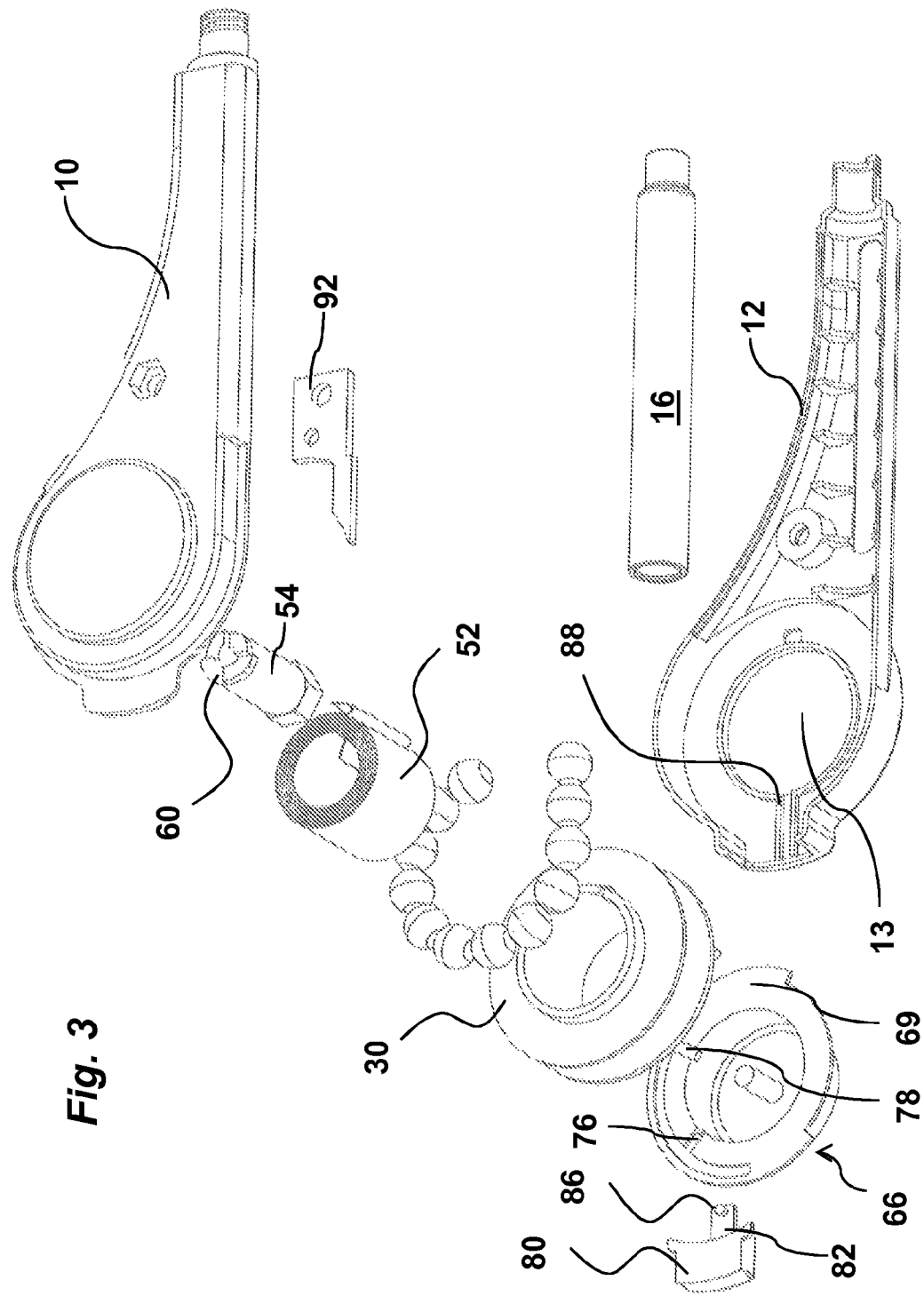
FIG. 3 is an exploded view of the device of FIG. 1 turned 180° in relation to FIG. 2, FIGS. 4-10 show side views of different functional positions of the device of FIG. 1.
Figure 4:
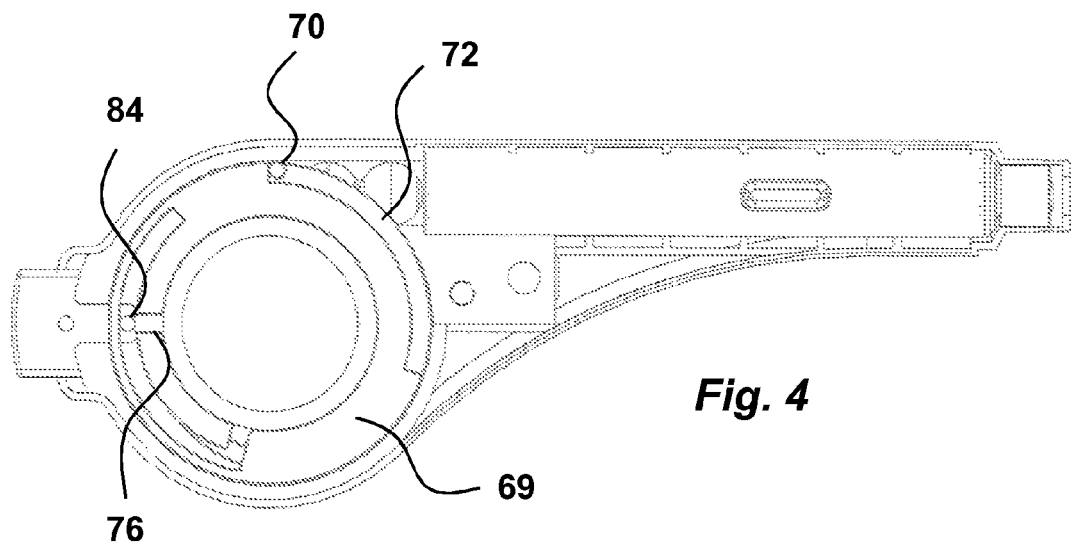
Figure 11A:
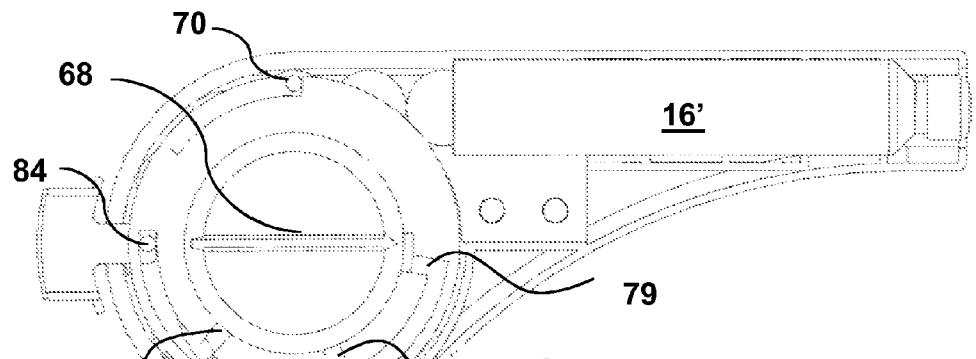
FIG. 11a is a side view of a second embodiment with a housing part of the device removed for clarity.
Figure 11B:
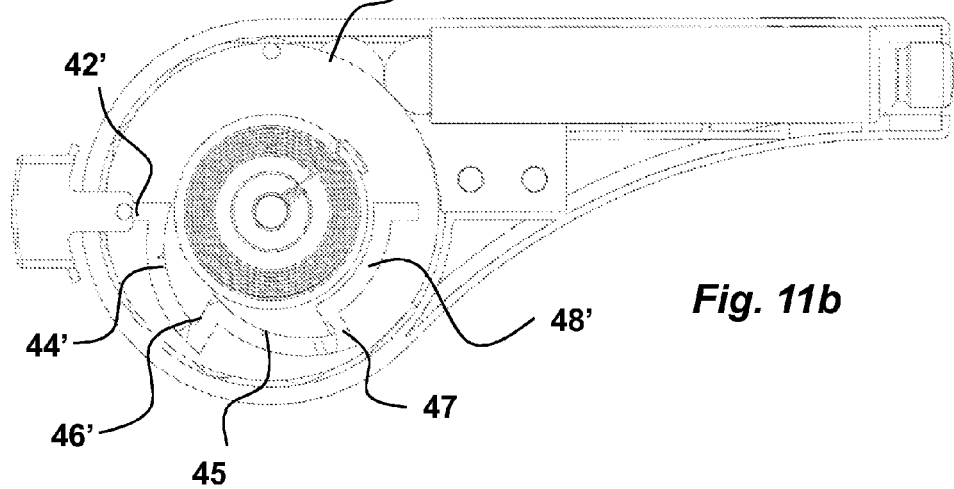
FIG. 11b is a side view of the embodiment of FIG. 11 with an activation wheel removed for clarity.
Figure 11C:
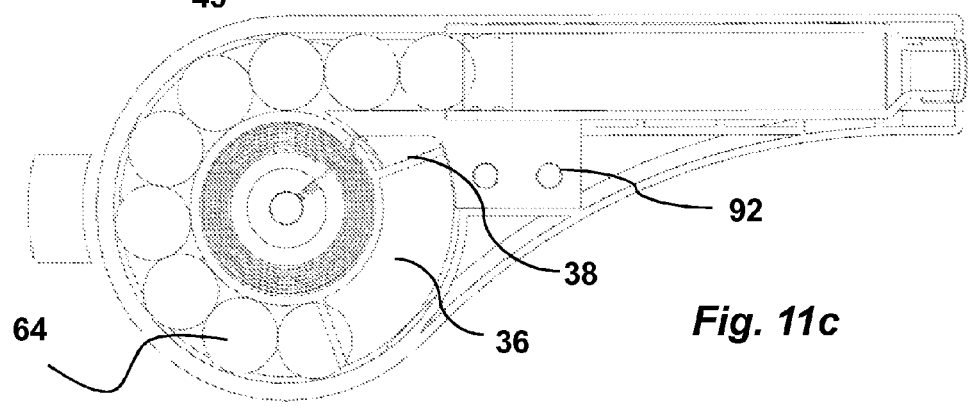
FIG. 11c is a cross-sectional side view of the device of FIG. 11a, and FIGS. 12-15 show side views of different functional positions of the device of FIG. 11.

The hold-and-release means, as shown in FIGS. 1b, 3 and 11b, being a first transversal protrusion 86 arranged on a proximally directed tongue 82 of the activation member 80, FIG. 3 and a first groove on the side surface of the first washer-formed disk 34; 34', said first groove comprising at least one first radially directed groove section 42, 46, FIG. 1b; 42', 46', 47, FIG. 11b, and at least one first generally circumferentially directed groove section 44, 48, FIG. 1b; 44', 45, 48', FIG. 11b, wherein each first radially directed groove section is followed by a first generally circumferentially directed groove section 44, 48; 44', 45, 48', as seen in FIGS. 1b and 11b, such that when said first transversal protrusion 86 is positioned in at least one first radially directed groove section, said support wheel and said clock spring are held in at least one tensioned and static state and when said activation member 80 is proximally moved from the non-depressed position to the depressed position, the first transversal protrusion 86 is moved from the at least one first radially directed groove section into the first generally circumferentially directed groove section, whereby the clock spring and thereby the support wheel are released from the at least one tensioned and static state. Further, each first generally circumferentially directed groove section 44, 48; 44', 45, 48' has a certain preset length corresponding to a preset dose quantity. It is however to be understood that other designs of the hold-and-release are feasible within the present invention.

In the first embodiment, as seen in FIG. 1b, the first groove is arranged with at least two first radially 42, 46 and at least two first generally circumferentially 44, 48 directed groove sections respectively, in succession, wherein the first of said first generally circumferentially directed groove sections 44 is arranged with an increasing radius for forcing said activation member 80 towards the distal direction from its depressed position to its non-depressed position, and wherein the last of said first generally circumferentially directed groove sections 48 is arranged with a constant radius, whereby said activation member is held in the depressed position, indicating that the device is used.

In the second embodiment, as seen in FIG. 11b, the first groove is arranged with a plurality of first radially 42', 46', 47 and first generally circumferentially 44', 45, 48' directed groove sections in succession providing the delivery of a plurality of doses of medicament, wherein the firsts of said first generally circumferentially directed groove sections 44', 45 are arranged with an increasing radius for forcing said activation member 80 towards the distal direction from its depressed position to its non-depressed position, and wherein the last of said first generally circumferentially directed groove sections 48' is arranged with a constant radius, whereby said activation member is held in the depressed position, indicating that the device is used.

In the first embodiment the medicament container 16 is of a so called dual chamber type, FIG. 1c, wherein said medicament container comprises two compartments 19, 20, each compartment containing a substance and being separated by a movable stopper 22, as well as by a distal stopper 24, wherein said first generally circumferentially directed groove section 44 enables the clock spring 52 to force the support wheel 30 and the plurality of spherical members 64 to perform a mixing of substances The medicament delivery device further comprises an activation wheel 66; 66' interactively connected to said activation member 80 by co-acting lock-and-release means such that when said activation member is in the non-depressed position, said lock-and-release means lock said activation member 80 from moving from its non-depressed position to its depressed position.

The activation wheel 66; 66' comprises a disk-shaped member 69; 69' arranged adjacent said support wheel 30; 30', as well as a grip means 68 for turning said activation wheel. The grip means 68 being adapted to extend through a circular opening 13 in the distal section of the second housing part 12.

The lock-and-release means, as shown in FIGS. 2, 3 and 11a, being a second transversal protrusion 84 arranged on the proximally directed tongue 82 of the activation member 80 and a second groove on the side surface of the disk-shaped member 69; 69', said second groove comprising a second generally circumferentially directed section 74; 74' and at least one second radially directed groove section 76, 78; 76', 78', 79, such that when said second transversal protrusion 84 is positioned in said second generally circumferentially directed section 74; 74', said activation member 80 is locked, and when second transversal protrusion 84 is positioned in front of one of said second radially directed groove sections 76, 78; 76', 78', 79, said activation member 80 may be moved from its non-depressed position to its depressed position.

As shown in FIGS. 1a and 12, the first washer-formed disk 34; 34' is provided with a third transversal protrusion 70 arranged to act on a cut-out 72 of said disk-shaped member 69; 69' such that when said support wheel 30, 30' is rotated by said clock spring 52, said third transversal protrusion 70 moves said activation wheel 66, 66' from a position allowing movement of said activation member 80 from its non-depressed position to its depressed position to a position where said activation member 80 is locked.

The device comes preferably delivered to the user with the medicament container 16, 16' placed inside the first compartment of the housing. Further the clock spring 52 has been pre-tensioned during assembly by rotating the one-direction-rotatable tubular hub 54 with a wrench or the like which engage the head 63 while the support wheel 30, 30' is held stationary. Due to the wedge-shaped surfaces 60, 62 of the one-direction-rotatable tubular hub 54 and the first housing part 10 respectively, turning of the one-direction-rotatable tubular hub 54 is only possible in one direction, but held locked against rotation in the opposite direction, whereby the clock spring 52 is held tensioned. The support wheel 30, 30' is held stationary by the first transversal protrusion 86 which is positioned in the first radially directed groove section 42; 42' of the first groove. Further, a distal second transversal protrusion 85 on the other side of the tongue 82 of the activation member 80 is positioned in a groove 88, FIG. 3, on the inner surface of the second housing part 12. In the non-depressed position, the activation member 80 is locked by the activation wheel 66, 66', which has a position such that the second transversal protrusion 84 of the activation member is in one end of the second generally circumferentially directed section 74, 74' of the second groove on the disk-shaped member 69; 69' of the activation wheel 66; 66' as seen in FIGS. 1a and 11b.

The device of the first embodiment, which comprises a dual-chamber container, is intended to function as follows. In order to activate the medicament delivery device and mix components inside the medicament container, the activation wheel 66 is turned in the clockwise direction by manually operating the grip means 68 until the third transversal protrusion 70 of the first washer-formed disk 34 abuts an end edge of the cut out 72 around the circumference of the disk-shaped member 69, FIG. 4. The second radially directed groove section 76 of the second groove on the disk-shaped member 69 of the activation wheel 66 is now in line with the second transversal protrusion 84 of the activation member, FIG. 4. This position could be indicated on the device by a window or opening 90 arranged on the second housing part 12, FIG. 2, and by a side surface of the a disk-shaped member 69 of the activation wheel 66 which is provided with indicia or different colours displaying a certain state. For instance, a green colour could indicate that the device is ready to be activated.

Figure 5A:
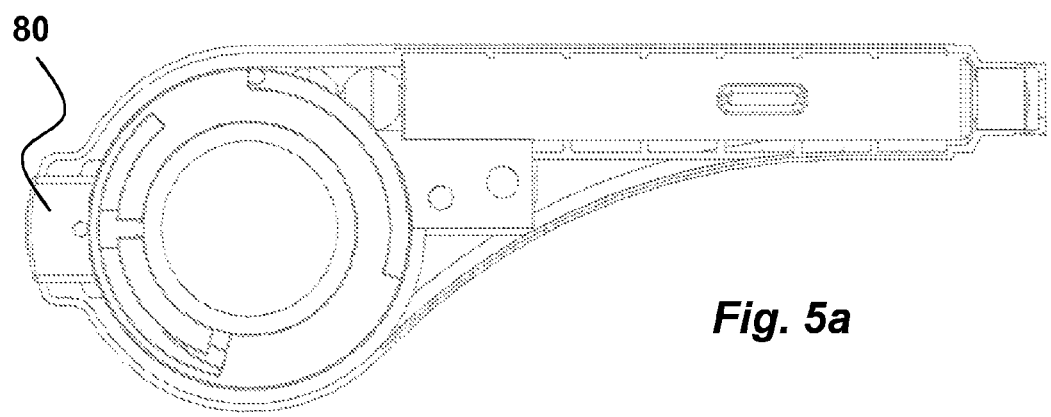
Figure 5B:
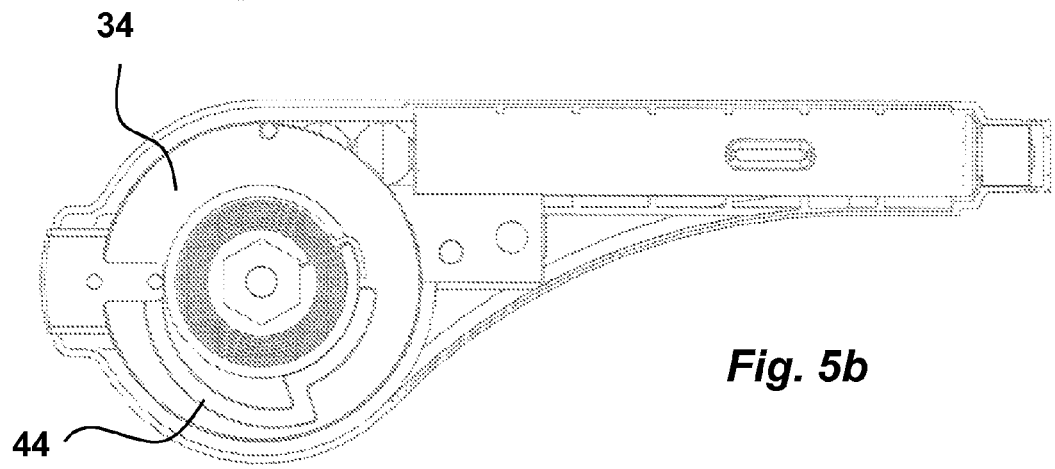

The activation member 80 can now be depressed in order to start the mixing operation, FIG. 5. This causes the second transversal protrusion 84 of the activation member to move along the second radially directed groove section 76 of the second groove on the disk-shaped member 69 of the activation wheel 66, and also the first transversal protrusion 86 on the other side of the tongue 82 to move along the first radially directed groove section 42 of the first groove on the first washer-formed disk 34 of the support wheel, which is held in a tensioned state by the clock spring 52. When the first transversal protrusion 86 has reached the end of the first radially directed groove section 42, FIG. 5c, and enters the first generally circumferentially directed groove section 44, the support wheel 30 is free to rotate in the clockwise direction by the force of the pre-tensioned clock spring 52. The cross-wall 38 of the support wheel 30 then acts on the balls 64, which in turn are moved and guided in the channel 28 towards the distal stopper 24. The distal stopper 24 is thus moved proximally towards the proximal stopper 22 such that they will be moved to a position where a passage is created between the two compartments 19, 20, whereby a mixing of the substances is performed, FIG. 8c.

Figure 6A:
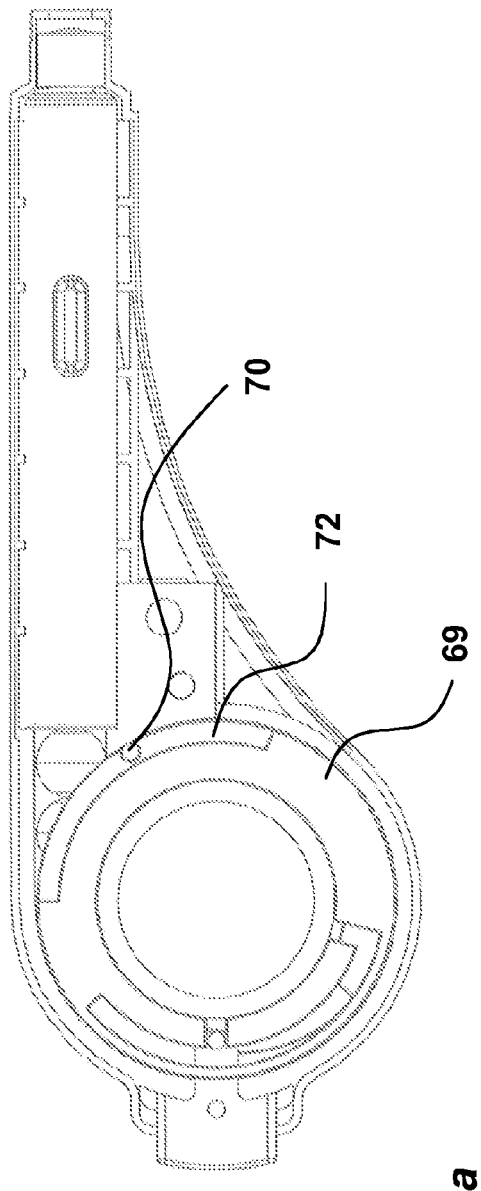
Figure 6B:
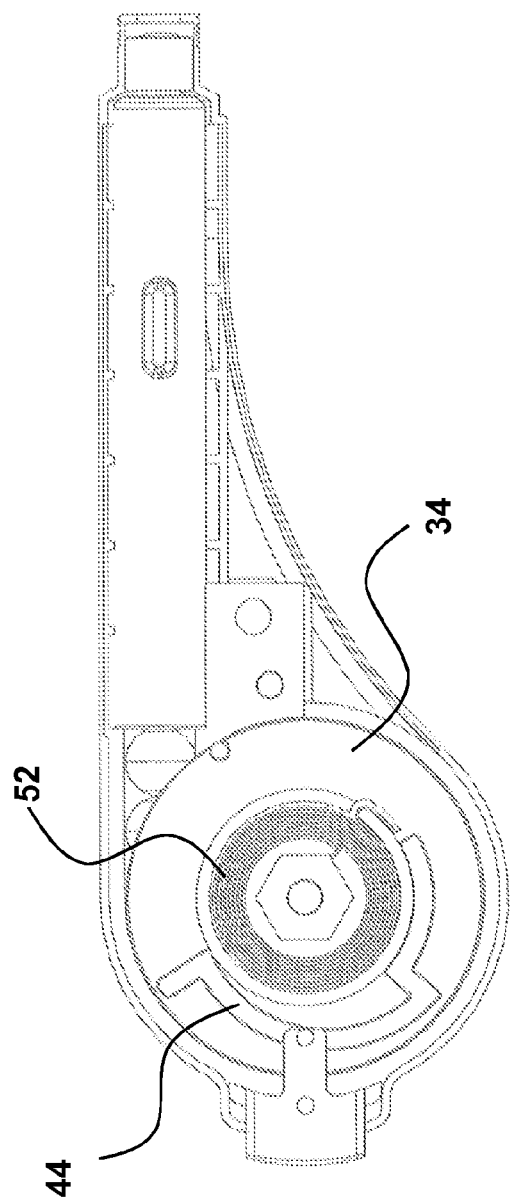
Figure 8A:
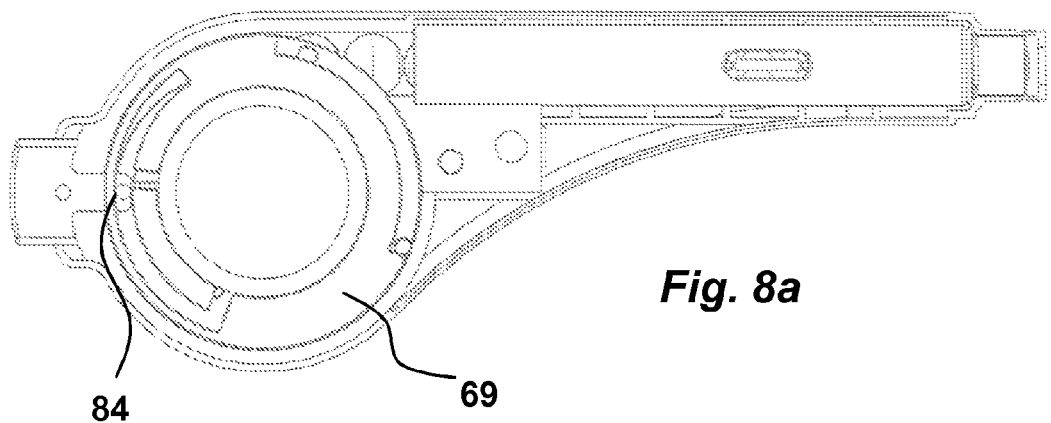
Figure 8B:
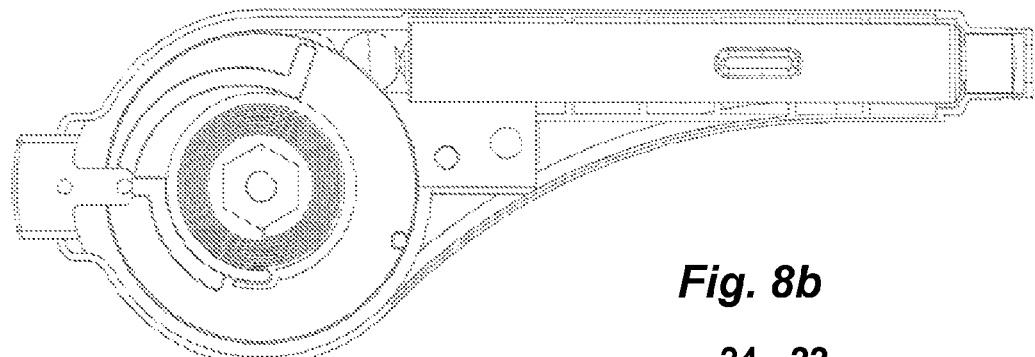
Figure 8C:
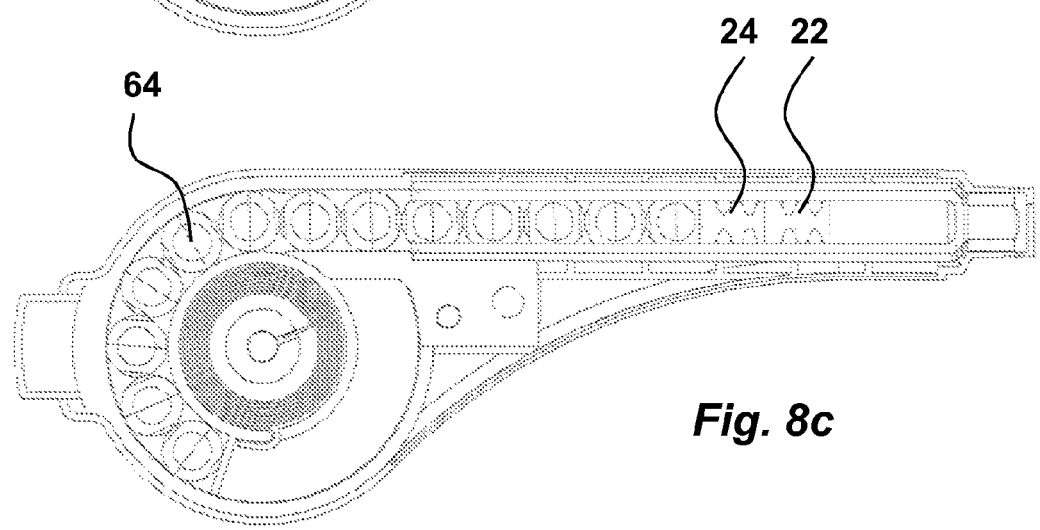
Figure 9:
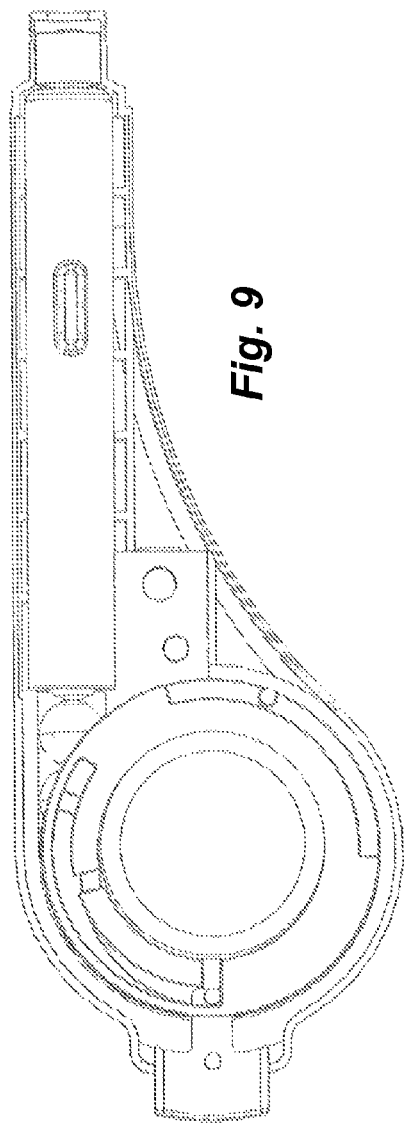
Figure 10A:
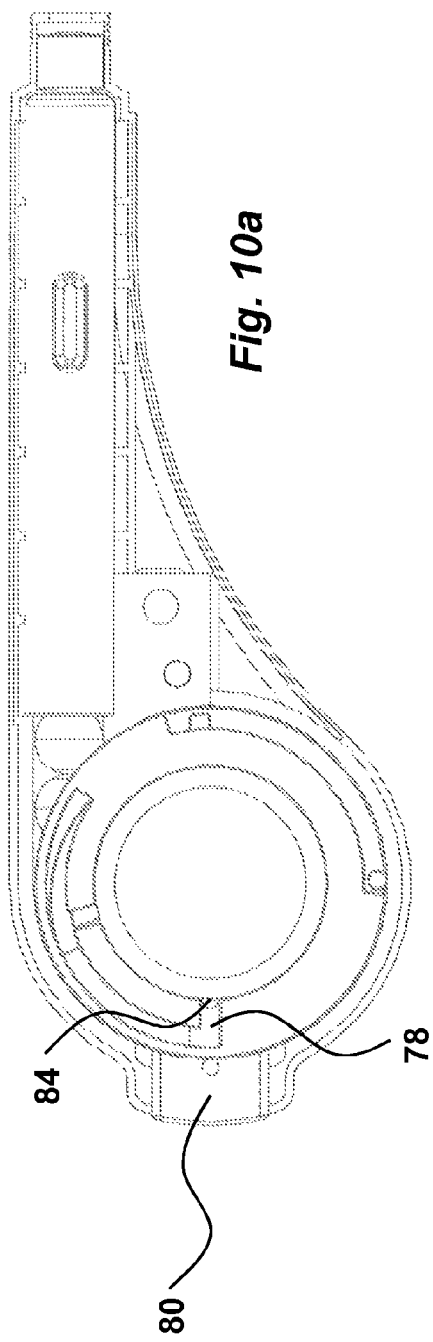
Figure 10B:
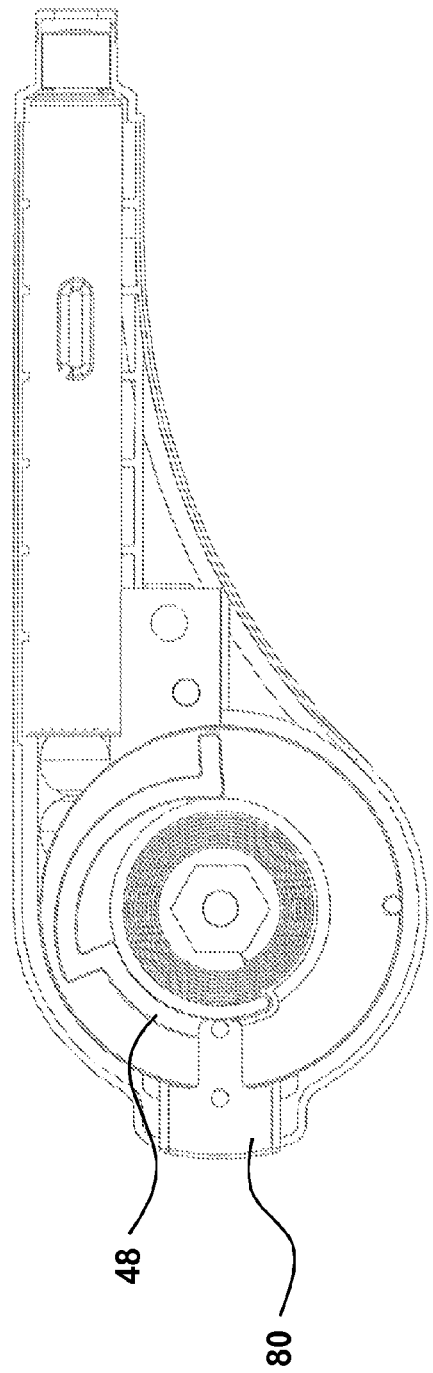
Figure 10C:
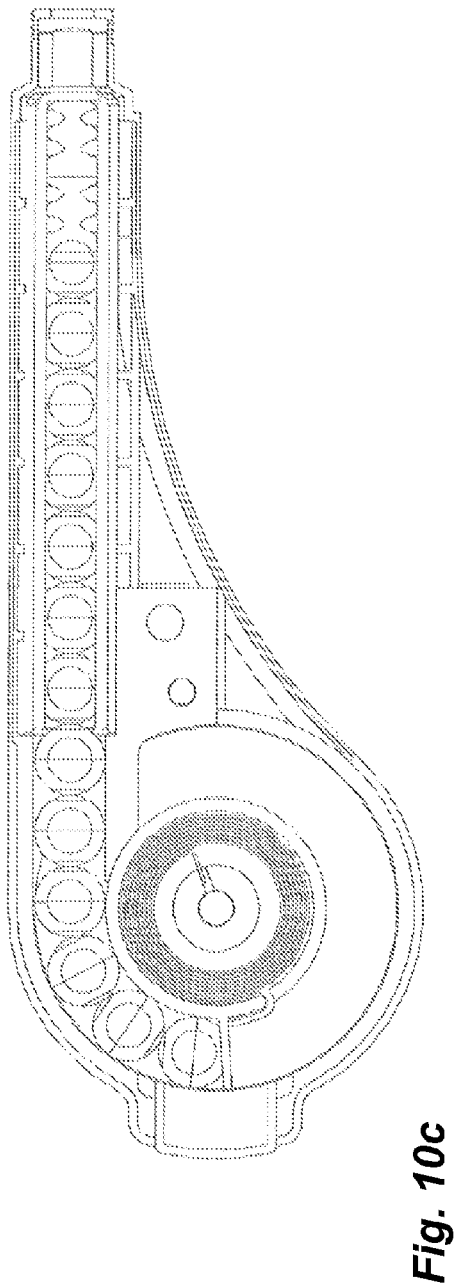

During the movement of the support wheel, the first transversal protrusion 86 of the activation member 80 is moved along the first generally circumferentially directed groove section 44, whereby the activation member is forced out in the distal direction, FIGS. 6 and 7, until the first transversal protrusion 86 hits an end surface of the first radially directed groove section 46, whereby the movement of the support wheel is stopped. During the movement of the support wheel, the third transversal protrusion 70 is also moved along the cut-out 72 until the third transversal protrusion 70 hits an end surface of the cut-out, FIG. 7a. The extent of the cut-out and position in relation to the position of the end surface of the first generally circumferentially directed groove section 44 is such that the activation wheel 66 is moved somewhat further such that the activation member 80 again is blocked from being depressed, FIG. 8a, by the second transversal protrusion 84 which is positioned in said second generally circumferentially directed section 74.

In order now to perform a medicament delivery, the device must again be activated. The activation wheel 66 is then manually turned again in the clockwise direction, whereby the second transversal protrusion 84 is moved in the second generally circumferentially directed section 74 until the second transversal protrusion 84 is in line with the second radially directed groove section 78 of the second groove on the disk-shaped member 69 of the activation wheel 66, FIG. 9. The activation member 80 may now be depressed. This may be shown in the window 90 by an appropriate indicia or colour.

The device is placed with its proximal end at the delivery site, which may be a penetration site if an injection needle is the delivery member. A penetration is then done manually. Thereafter the activation member 80 is depressed whereby the second transversal protrusion 84 is moved in the second radially directed groove section 78, FIG. 10a, such that the first transversal protrusion 86 is also moved in the first radially directed groove section 46 of the first groove on the first washer-formed disk 34 of the support wheel 30 until the first transversal protrusion 86 comes to the first generally circumferentially directed groove section 48, FIG. 10b, such that the support wheel 30 starts to rotate in the clockwise direction by the force of the clock spring 52. Again the movement of the support wheel causes the balls 64 to be moved in the proximal direction, pushing the stoppers 22, 24 in front of them such that a dose of medicament is expelled through the medicament delivery member. The movement of the support wheel 30 is stopped when the stoppers have reached the proximal end position inside the medicament container, FIG. 10c. Since the first generally circumferentially directed groove sections 48 is arranged with a constant radius, then said activation member is held in the depressed position, FIG. 10b, indicating that the device is used and that can be discarded. There is thus no risk that a user later mixes up used and unused devices.

The device of the second embodiment, which comprises a single chamber medicament container 16' containing a number of doses to be delivered, is intended to function as follows. A medicament delivery member is attached to the proximal neck portion of the housing. In order to deliver a dose of medicament, the activation wheel 66' is turned in the clockwise direction by manually operating the grip means 68 until the third transversal protrusion 70 of the first washer-formed disk 34' abuts an end edge of the cut out 72 around the circumference of the disk-shaped member 69'. The second radially directed groove section 76' of the second groove on the disk-shaped member 69' of the activation wheel 66' is now in line with the second transversal protrusion 84 of the activation member. This position could be indicated on the device by a window or opening 90 arranged on the second housing part 12 and by a side surface of the a disk-shaped member 69' of the activation wheel 66' which is provided with indicia or different colours displaying a certain state. For instance, a green colour could indicate that the device is ready to be activated.

The device is placed with its proximal end at the delivery site, which may be a penetration site if an injection needle is the delivery member. A penetration is then done manually. The activation member 80 can now be depressed in order to start the delivery operation. This causes the second transversal protrusion 84 of the activation member to move along the second radially directed groove section 76' of the second groove on the disk-shaped member 69' of the activation wheel 66', and also the first transversal protrusion 86 on the other side of the tongue 82 to move along the first radially directed groove section 42' of the first groove on the first washer-formed disk 34' of the support wheel 30', which is held in a tensioned state by the clock spring 52. When the first transversal protrusion 86 has reached the end of the first radially directed groove section 42' and enters the first generally circumferentially directed groove section 44', FIG. 13, the support wheel 30' is free to rotate in the clockwise direction by the force of the pre-tensioned clock spring 52. The cross-wall 38 of the support wheel 30' then acts on the balls 64, which in turn are moved and guided in the channel 28 towards the distal stopper 24. The distal stopper 24 is thus moved proximally such that a dose of medicament is expelled through the medicament delivery member. The medicament delivery member is now removed.

Figure 14A:
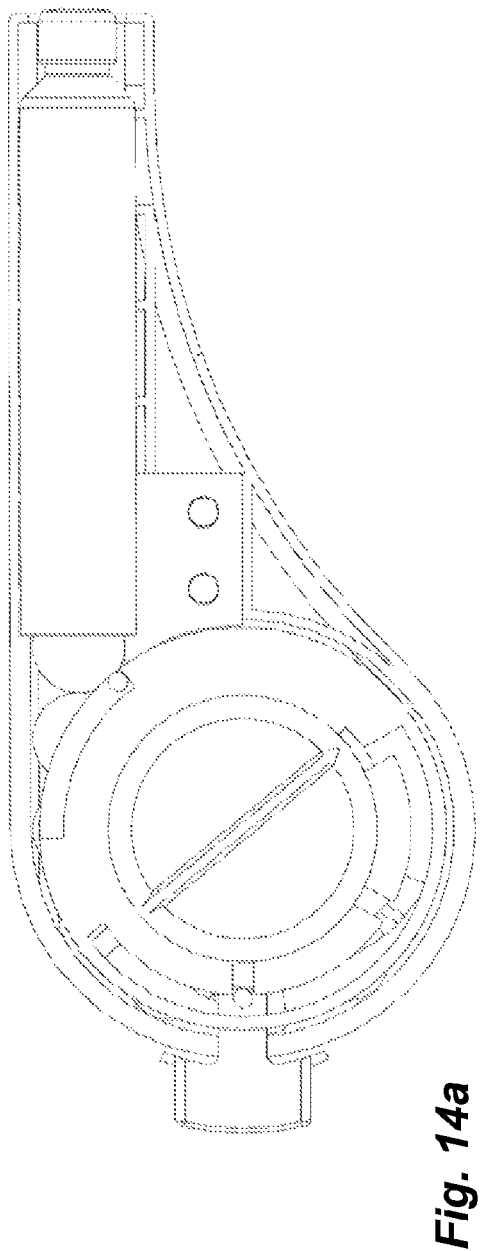
Figure 14B:
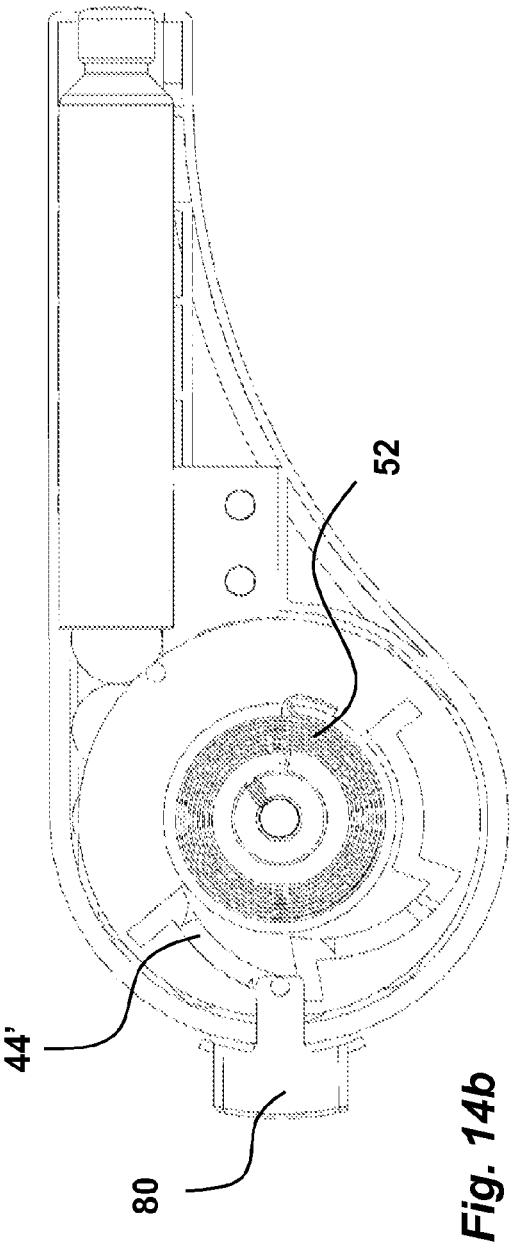

During the movement of the support wheel, the first transversal protrusion 86 of the activation member 80 is moved along the first generally circumferentially directed groove section 44', whereby the activation member is forced out in the distal direction, FIGS. 14a and 14b, until the first transversal protrusion 86 hits an end surface of the first radially directed groove section 46', whereby the movement of the support wheel is stopped. During the movement of the support wheel, the third transversal protrusion 70 is also moved along the cut-out 72 until the third transversal protrusion 70 hits an end surface of the cut-out, FIG. 14a. The extent of the cut-out and position in relation to the position of the end surface of the first generally circumferentially directed groove section 44' is such that the activation wheel 66' is moved somewhat further such that the activation member 80 again is blocked from being depressed, FIG. 15a, by the second transversal protrusion 84 which is positioned in said second generally circumferentially directed section 74'.

When the device is to be used a subsequent time, a new medicament delivery member is attached and the above operation is performed. As seen from the design of the groove sections of the first groove on the first washer-formed disk 34 of the support wheel 30' and of the groove sections of the second groove on the disk-shaped member 69' of the activation wheel 66', three doses may be delivered and after the last dose delivery the protrusion 86 will enter in the first generally circumferentially directed groove section 48' of the first groove on the first washer-formed disk 34 of the support wheel whereby the activation member is locked, indicating that the medicament container is empty. From the above it is clear that the groove sections on the first washer-formed disk 34' of the support wheel 30' and the groove sections on the disk-shaped member 69' of the activation wheel 66' may be modified to provide more doses to be delivered.

It is to be understood that the embodiment described above and shown in the drawings is to be regarded only as a non-limiting example of the present invention and that it may be amended in many ways within the scope of the patent claims.

The invention claimed is:

1. A medicament delivery device, comprising:
   a housing having a proximal section and a distal section formed by a first housing part and a second housing part;
   a first compartment inside the proximal section for accommodating a medicament container that includes at least one stopper;
   a circle-segment-shaped second compartment inside the distal section for accommodating a drive unit configured for moving the at least one stopper in a proximal direction within the medicament container;
   wherein the drive unit comprises:
      a support wheel rotatably arranged inside the second compartment and comprising a central tubular hub on which first and second washer-shaped disks are fixedly attached in parallel to each other and interconnected by an abutment cross-wall;
      a plurality of spherical members arranged in a row between the abutment wall and adjacent the stopper, the plurality of spherical members being guided in a channel formed by an inner periphery of the circle-segment-shaped second compartment, by an outer periphery of the central tubular hub, by inner side surfaces of the washer-shaped disks, and by a guide member;
      a pre-tensioned clock spring coaxially arranged within the central tubular hub and having an outer end connected to the central tubular hub and an inner end connected to a one-direction-rotatable tubular hub coaxially arranged around a shaft fixedly attached to the first housing part; and
      an activation member interactively connected to the first washer-shaped disk by a co-acting hold-and-release mechanism, such that when the activation member is in a non-depressed position, the support wheel and clock spring are held in at least one tensioned and static state, and when the activation member is moved from the non-depressed position to a depressed position, the clock spring and thereby the support wheel are released from the at least one tensioned and static state such that the plurality of spherical members are forced against the at least one stopper.

2. The medicament delivery device of claim 1, wherein the hold-and-release mechanism includes a first transversal protrusion arranged on a proximally directed tongue of the activation member, and a first groove on the side surface of the first washer-shaped disk, the first groove comprising at least one first radially directed groove section and at least one first generally circumferentially directed groove section, wherein each first radially directed groove section is followed by a first generally circumferentially directed groove section, such that when the first transversal protrusion is positioned in at least one first radially directed groove section, the support wheel and clock spring are held in at least one tensioned and static state, and when the activation member is proximally moved from the non-depressed position to the depressed position, the first transversal protrusion is moved from the at least one first radially directed groove section into the first generally circumferentially directed groove section, whereby the clock spring and thereby the support wheel are released from the at least one tensioned and static state.

3. The medicament delivery device of claim 2, wherein each first generally circumferentially directed groove section has a preset length corresponding to a preset dose quantity.

4. The medicament delivery device of claim 3, wherein the first groove is arranged with at least two first radially directed groove sections and at least two first substantially circumferentially directed groove sections, in succession, wherein a first one of the first generally circumferentially directed groove sections has an increasing radius configured for forcing the activation member toward the distal direction from its depressed position to its non-depressed position, and a last one of the first generally circumferentially directed groove sections has a constant radius, whereby the activation member is held in the depressed position, indicating that the device is used.

5. The medicament delivery device of claim 4, further comprising an activation wheel interactively connected to the activation member by the co-acting lock-and-release mechanism such that when the activation member is in the non-depressed position, the lock-and-release mechanism locks the activation member from moving from its non-depressed position to its depressed position.

6. The medicament delivery device of claim 5, wherein the activation wheel comprises a disk-shaped member adjacent the support wheel, and a grip device configured for turning the activation wheel.

7. The medicament delivery device of claim 6, wherein the lock-and-release mechanism includes a second transversal protrusion arranged on the proximally directed tongue of the activation member, and a second groove on the side surface of the disk-shaped member, the second groove comprising a second substantially circumferentially directed section and at least one second radially directed groove section, such that when the second transversal protrusion is positioned in the second substantially circumferentially directed section, the activation member is locked, and when the second transversal protrusion is positioned in front of one of the second radially directed groove sections, the activation member is movable from its non-depressed position to its depressed position.

8. The medicament delivery device of claim 7, wherein the first washer-shaped disk has a third transversal protrusion arranged to act on a cut-out of the disk-shaped member, such that when the support wheel is rotated by the clock spring, the third transversal protrusion moves the activation wheel from a position allowing movement of the activation member from its non-depressed position to its depressed position, to a position where the activation member is locked.

9. The medicament delivery device of claim 4, wherein the medicament container comprises two compartments, each compartment containing a respective substance and being separated by a movable stopper and by a distal stopper; a first substantially circumferentially directed groove section enables the clock spring to force the support wheel and plurality of spherical members to mix the substances.

10. The medicament delivery device of claim 3, further comprising an activation wheel interactively connected to the activation member by the co-acting lock-and-release mechanism such that when the activation member is in the non-depressed position, the lock-and-release mechanism locks the activation member from moving from its non-depressed position to its depressed position.

11. The medicament delivery device of claim 10, wherein the activation wheel comprises a disk-shaped member adjacent the support wheel, and a grip device configured for turning the activation wheel.

12. The medicament delivery device of claim 11, wherein the lock-and-release mechanism includes a second transversal protrusion arranged on the proximally directed tongue of the activation member, and a second groove on the side surface of the disk-shaped member, the second groove comprising a second substantially circumferentially directed section and at least one second radially directed groove section, such that when the second transversal protrusion is positioned in the second substantially circumferentially directed section, the activation member is locked, and when the second transversal protrusion is positioned in front of one of the second radially directed groove sections, the activation member is movable from its non-depressed position to its depressed position.

13. The medicament delivery device of claim 12, wherein the first washer-shaped disk has a third transversal protrusion arranged to act on a cut-out of the disk-shaped member, such that when the support wheel is rotated by the clock spring, the third transversal protrusion moves the activation wheel from a position allowing movement of the activation member from its non-depressed position to its depressed position, to a position where the activation member is locked.

14. The medicament delivery device of claim 3, wherein the first groove has a plurality of first radially directed groove sections and first generally circumferentially directed groove sections, in succession, configured for delivery of a plurality of doses of medicament, wherein first ones of the first generally circumferentially directed groove sections have increasing radii for forcing the activation member toward the distal direction from its depressed position to its non-depressed position, and a last one of the first generally circumferentially directed groove sections has a constant radius, whereby the activation member is held in the depressed position, indicating that the device is used.

15. The medicament delivery device of claim 2, further comprising an activation wheel interactively connected to the activation member by the co-acting lock-and-release mechanism such that when the activation member is in the non-depressed position, the lock-and-release mechanism locks the activation member from moving from its non-depressed position to its depressed position.

16. The medicament delivery device of claim 15, wherein the activation wheel comprises a disk-shaped member adjacent the support wheel, and a grip device configured for turning the activation wheel.

17. The medicament delivery device of claim 16, wherein the lock-and-release mechanism includes a second transversal protrusion arranged on the proximally directed tongue of the activation member, and a second groove on the side surface of the disk-shaped member, the second groove comprising a second substantially circumferentially directed section and at least one second radially directed groove section, such that when the second transversal protrusion is positioned in the second substantially circumferentially directed section, the activation member is locked, and when the second transversal protrusion is positioned in front of one of the second radially directed groove sections, the activation member is movable from its non-depressed position to its depressed position.

18. The medicament delivery device of claim 17, wherein the first washer-shaped disk has a third transversal protrusion arranged to act on a cut-out of the disk-shaped member, such that when the support wheel is rotated by the clock spring, the third transversal protrusion moves the activation wheel from a position allowing movement of the activation member from its non-depressed position to its depressed position, to a position where the activation member is locked.

* * * * *